(12) United States Patent
Belcher et al.

(10) Patent No.: US 7,332,321 B2
(45) Date of Patent: Feb. 19, 2008

(54) VIRAL FIBERS

(75) Inventors: Angela M. Belcher, Lexington, MA (US); Seung-Wuk Lee, Cambridge, MA (US)

(73) Assignees: Board of Regents, The University of Texas System, Austin, TX (US); Massachusetts Institute of Technology, Cambridge, MA (US)

( * ) Notice: Subject to any disclaimer, the term of this patent is extended or adjusted under 35 U.S.C. 154(b) by 2 days.

(21) Appl. No.: 10/965,665

(22) Filed: Oct. 15, 2004

(65) Prior Publication Data

US 2005/0180992 A1 Aug. 18, 2005

Related U.S. Application Data

(60) Provisional application No. 60/510,862, filed on Oct. 15, 2003.

(51) Int. Cl.
*C12N 7/01* (2006.01)
*D01F 8/18* (2006.01)
*D02G 3/04* (2006.01)

(52) U.S. Cl. .............. 435/235.1; 435/317.1; 442/123; 57/295

(58) Field of Classification Search ............. 424/204.1, 424/443; 435/5, 235.1, 7.1, 6, 7.2; 442/123
See application file for complete search history.

(56) References Cited

U.S. PATENT DOCUMENTS

| | | | |
|---|---|---|---|
| 5,223,409 A | 6/1993 | Ladner et al. |
| 5,403,484 A | 4/1995 | Ladner et al. |
| 5,571,698 A | 11/1996 | Ladner et al. |
| 5,766,905 A | 6/1998 | Studier et al. |
| 5,885,808 A | 3/1999 | Spooner et al. |
| 6,106,913 A | 8/2000 | Scardino et al. |
| 6,110,590 A | 8/2000 | Zarkoob et al. |
| 6,261,554 B1 | 7/2001 | Valerio et al. |
| 6,308,509 B1 | 10/2001 | Scardino et al. |
| 6,382,526 B1 | 5/2002 | Reneker et al. |
| 6,520,425 B1 | 2/2003 | Reneker et al. |
| 6,616,435 B2 | 9/2003 | Lee et al. |
| 2001/0019820 A1 | 9/2001 | Li et al. |
| 2003/0068900 A1 | 4/2003 | Belcher et al. |
| 2003/0073104 A1 | 4/2003 | Belcher et al. |
| 2003/0113714 A1 | 6/2003 | Belcher et al. |
| 2003/0148380 A1 | 8/2003 | Belcher et al. |
| 2004/0127640 A1 | 7/2004 | Belcher et al. |
| 2004/0171139 A1 | 9/2004 | Belcher et al. |
| 2005/0064508 A1 | 3/2005 | Belcher et al. |

OTHER PUBLICATIONS

Matsuno et al., "Orientations of Tyrosines 21 and 24 in Coat Subunits of Ff Filamentous Virus: Determination by Raman Linear intensity Difference Spectroscopy and Implications for Subunit Packing," Biophysical Journal, vol. 74, pp. 3217-3225 (1998).*

Ober, "Persistence Pays Off," Science, vol. 296, pp. 859, 861 (2002).*
Zhao et al., "Purification and Characterization of the Fusion Protein Trypsin-Streptavidin Expressed in *Escherichia coli*," Journal of Protein Chemistry, vol. 21, No. 6, (2002).*
Aizenberg, J., et al., "Direct Fabrication of Large Micropatterned Single Crystals", Science, vol. 299, pp. 1205-1208 (2003).
Alivisatos, A. P., et. al., "Organization of 'nanocrystal molecules' of DNA", Nature, vol. 382, pp. 609-611 (1996).
Ball, P., "It all falls into place . . . ", Nature, vol. 413, pp. 667-668 (2001).
Belcher, A.M., et al., "Control of Crystal Phase Switching and Orientation by Soluble Mollusc-Shell Proteins", NATURE, vol. 381, No. 6577, pp. 56-58 (1996).
Berghoef, M. M., et al.., Transparent Nanocomposites with Ultrathin, Electrospun Nylon-4,6 Fiber Reinforcement, Adv. Mat., vol. 11, No. 16, pp. 1362-1365 (1999).
Billmeyer, F. W., *Textbook of Polymer Science*, 3$^{rd}$ edition, chptr. 18, p. 486-505 (1984).
Bognitzki, M., et . al., "Nanostructured Fibers via Electrospinning", Adv. Mat., vol. 13, No. 1, p. 70-72 (2001). Bognitzki, M., et. al., "Preparation of Fibers With Nanoscaled Morphologies: Electrospinning of Polymer Blends", Pol. Eng. & Sci., vol. 41, No. 6, pp. 982-989 (2001).
Brown, S., "Metal-recognition by repeating polypeptides", Nature Biotechnology, vol. 15, pp. 269-272 (1997).
Cha, J. N., et al., "Biomimetic synthesis of ordered silica structures mediated by block copolypeptides", Nature, vol. 403, No. 20, pp. 289-292 (2000).
Cölfen, H., et al., "Higher-Order Organization by Mesoscale Self-Assembly and Transformation of Hybrid Nanostructures", Angew. Chem. Int. Ed., vol. 42, pp. 2350-2365 (2003).
Dogic, Z., et. al., "Smectic Phase in a Colloidal Suspension of Semiflexible Virus Particles", Phy. Rev. Letts., vol. 78, No. 12, pp. 2417-2420 (1997).
Doshi, J., et. al., "Electrospinning Process and Applications of Electrospun Fibers", J. Electro., vol. 35, pp. 151-160 (1995).
Douglas, D., et. al., "Host-guest encapsulation of materials by assembled virus protein cages", Nature, vol. 393, p. 152-155 (1998).
Flynn, C. E., et. al., "Synthesis and organization of nanoscale II-VI semiconductor materials using evolved peptide specificity and viral capsid assembly", J. Mater. Chem., vol. 13, pp. 2414-2421 (2003).

(Continued)

*Primary Examiner*—Mary E. Mosher
(74) *Attorney, Agent, or Firm*—Foley & Lardner LLP

(57) ABSTRACT

Long rod shaped M13 viruses were used to fabricate one dimensional (1D) micro- and nanosized diameter fibers by mimic the spinning process of the silk spider. Liquid crystalline virus suspensions were extruded through the micrometer diameter capillary tubes in cross-linking solution (glutaraldehyde). Resulting fibers were tens of micrometers in diameter depending on the inner diameter of the capillary tip. AFM image verified that molecular long axis of the virus fibers were parallel to the fiber long axis. Although aqueous M13 virus suspension could not be spun by electrospinning, M13 viruses suspended in 1,1,1,3,3,3-hexafluoro-2-propanol were spun into fibers. After blending with highly water soluble polymer, polyvinyl 2-pyrolidone (PVP), M13 viruses was spun into continuous uniform virus blended PVP (virus-PVP) fibers. Resulting virus-PVP electrospun fibers showed intact infecting ability to bacterial hosts after suspending in the buffer solution.

28 Claims, 13 Drawing Sheets

OTHER PUBLICATIONS

Flynn, C.E., et. al., "Viruses as vehicles for growth, organization and assembly of materials", Acta Mater., vol. 51, pp. 5867-5880 (2003).

Forest, M. G., et al., "Model Study of the Spinning of Thermotropic Liquid Crystalline Polymers: Fibert Performance Predictions and Bounds on Throughput",Adv. Poly. Tech., vol. 18, No. 4, pp. 314-335 (1999).

Hartgerink, J. D., et al., "Self-Assembly and Mineralization of Peptide-Amphiphile Nanofibers", Science, vol. 294, pp. 1684-1688 (2001).

Hayashi, C. Y., et al., "Evidence from Flagelliform Silk cDNA for the Structural Basis of Elasticity and Modular Nature of Spider Silks", J. Mol. Biol., vol. 275, pp. 773-784 (1998).

Hayashi, C. Y., et. al., "Molecular Architecture and Evolution of a Modular Spider Silk Protein Gene", Science, vol. 287, pp. 1477-1479 (2002).

Hohman, M. M., et. al, "Electrospinning and electrically forced jets. I. Stability theory", Phys. Fluids, vol. 13, No. 8, pp. 2201-2220 (2001).

Huang, L., et. al., "Generation of Synthetic Elastin-Mimetic Small Diameter Fibers and Fiber Netowrks", Macromolecules, vol. 33, pp. 2989-2997 (2000).

Huang, M. H., et al., "Room-Temperature Ultraviolet Nanowire Nanolasers", Science, vol. 292, pp. 1897-1899 (2001).

Jin, H., et. al., "Electrospinning Bombyx mori Silk with Poly(ethylene oxide)", Biomacromolecules, vol. 3, pp. 1233-1239 (2002).

Kroschwitz (editor). *Concise Encyclopedia of Polymer Science and Engineering*, "Fibers", pp. 374-395, date not available.

Lee, S., et. al., "Chiral Smectric C Structures of Virus-Based Films", Langmuir, vol. 19, No. 5, pp. 1592-1598 (2003).

Lee, S., et al., "Ordering of Quantum Dots Using Geneticallly Engineered Viruses", Science, vol. 296, pp. 892-895 (2002).

Lee, S., et. al., "Virus-Based Alignment of Inorganic, Organic, and Biological Nanosized Materials", Adv. Mater., vol. 15, No. 9, pp. 689-692 (2003).

Lee, S., Doctoral Thesis, "Self-assembly of Nanomaterials into Films and Fibers Using Genetically Engineered Virguses", Chptr. 5, pp. 116-135, The University of Texas, Austin (2003).

Lee, S., et. al., "Virus-Based Fabrication of Micro- and Nanofibers Using Electrospinning", Nano Letts., vol. 4, No. 3, pp. 387-390 (2004).

Li, D., et. Al., "Fabrication of Titania Nanofibers by Electrospinning", Nano Letts., vol. 3, No. 4, pp. 555-560 (2003).

Li, D., et. al., "Electrospinning of Polymeric and Ceramic Nanofibers as Uniaxially Aligned Arrays", Nano Letts., vol. 3, No. 8, pp. 1167-1171 (2003).

Li, L., et. al., "Semiconductor Nanorod Liquid Crystals and Their Assembly on a Substrate", Adv. Mater., vol. 15, No. 5, pp. 408-411 (2003).

Mao, C., et. al., "Viral Assembly of oriented quantum dot nanowires", PNAS, vol. 100, No. 12, pp. 6946-6951 (2003).

Mao, C., et al., "Virus-Based Toolkit for the Directed Synthesis of Magnetic and Semiconducting Nanowires", Science, vol. 303, pp. 213-217 (2004).

Matthews, J. A., et. al., "Electrospinning of Collagen Nanofibers", Biomacromolecules, vol. 3, pp. 232-238 (2002).

Megelski, S., et. al., "Micro- and Nanostructured Suface Morphology on Electrospun Polymer Fibers", Macromolecules, vol. 35, pp. 8456-8466 (2002).

Mirkin, C., et. al., "A DNA-based method for rationally assemblying nanoparticles into macroscopic materials", Nature, vol. 382, pp. 607-609 (1996).

Nygaard, S., et. al., "Surface-Specific Zeolite-Binding Proteins", Adv. Mater.vol. 14, No. 24, pp. 1853-1856 (2002).

Rueckes, T., et. al., "Carbon Nanotube-Based Nonvolatile Random Access Memory for Molecular Computing", Science, vol. 289, pp. 94-97 (2000).

Seeman, N. C., "DNA in a material world", Nature, vol. 421, pp. 427-431 (2003).

Taylor, G., et. al., "Electrically drive jets", Proceedings of Royal Society London A, vol. 313, pp. 453-475 (1969).

Valluzi, R., et. al., "Silk: molecular organization and control of assembly", Phil. Trans. R. Soc. Lond. B, vol. 357, pp. 165-167 (2002).

Vollrath, F., et. al., "Liquid crystalline spinning of spider silk", Nature, vol. 410, pp. 541-548 (2001).

Wang, X., et. al., "Electrospun Nanofibrous Membrances for Highly Sensitive Optical Sensors", Nano Letts., vol. 2, No. 11, pp. 1273-1275 (2002).

Whaley, S. R,. et. al., "Selection of peptides with semiconductor binging specificity for directed nanocrystal assembly", Nature, vol. 405, pp. 665-668 (2000).

Wnek, G. E., et. al., "Electrospinning of Nanofiber Fibrinogen Structures", Nono Letts., vol. 3, no. pp. 213-216 (2003).

Yao, Z., et. al., "Carbon Nanotube intramolecular junctions", Nature, vol. 402, pp. 273-276 (1999).

* cited by examiner (A)  (B)  (C)  (D)

(A)                    (B)

(A)

(B)

(A) (B) (C)

(D) (E)

(A)

(B)

(A)

(B)

VIRAL FIBERS

CROSS-REFERENCE TO RELATED PATENT APPLICATIONS

This application claims benefit to provisional application 60/510,862 filed Oct. 15, 2003 to Belcher et al., which is hereby incorporated by reference in its entirety.

This invention was developed under the following grants from the federal government: Grant No. DAAD19-03-1-0088, from the Army Research Office. The government has certain rights in the invention.

INTRODUCTION

The introduction section provides reference to a number of technical publications which are found at the end of the specification and can be used as a guide to one skilled in the art to practice the present invention. No admission is made that any of these references are indeed prior art.

Efforts to mimic the unique structures and specific functions of natural systems have provided various useful tools and materials in nanoscience [1-14]. Biosystems produce highly programmed, self-assembled, self-templated structures [6-11]. For example, a small percentage of protein in abalone shell nucleates a CaCO3 protein composite that is 3000 times tougher than pure CaCO3 [1]. By mimicking the biomineralization process in nature, it has been shown that protein sequences, selected through fast evolution of a genetically engineered virus library on the bench top, can specifically bind to and nucleate desired materials [3-7]. The one-pot synthetic route provided by these genetically programmed viruses results in self-assembled, highly ordered nanocrystal composite materials [4].

The unique properties of biological materials are not limited to their structures and functions. Silk spiders and silk worms spin highly engineered continuous fibers by passing aqueous liquid crystalline protein (fibroin) solution through their spinneret [15-18]. Once the fibroin solution is released to the air, it hardens into a flexible and highly oriented semicrystalline fiber that is stronger than any other polymer fiber spun [17].

Recently, much research has been focused on producing nanosized one-dimensional materials such as nanorods, nanowires, and nanofibers [19-24], as well as two- and three-dimensional materials. Among them, nanofiber fabrication using electrospinning has been an efficient means of generating high surface-to-volume ratios of materials that may possibly be used as highly sensitive sensors, functional membranes, tissue repair applications, and mechanical structures. Electrospinning is a process of using high electric fields to make narrow fibers with diameters ranging from tens of nanometers to micrometers [23-27]. When an electric field is applied to suspensions extruded through a narrow spinneret, an electrostatically charged hemispherical liquid surface at the tip of the spinneret is elongated and forms a conical surface known as Taylor cone [27]. As the electric field is increased to a critical value, the suspension is violently ejected from the conical surface to the grounded collecting plates. The ejected fibers randomly separate and quickly dry to form narrow diameter fibers. Depending on parameters, such as the electric field applied, distance between tip and collector, and viscosity and conductivity of the suspension, micro- or nanometer scale fibers can be fabricated. The distance between the tip and grounded collecting plate is roughly inversely proportional to the diameter of the fibers because greater chances of fiber separation exist during flight [28,29]. Concentration, which directly affects the viscosity of the suspension, can play an important role in electrospinning. Below a particular concentration, suspensions at times are electrosprayed and not electrospun, resulting in deposited droplets of suspension. As this concentration is approached, bead and string shaped fibers are formed [29-30]. Increasing the concentration results in the formation of continuous fibers. However, above an upper concentration limit, the solution at times becomes too viscous to be pulled by electrostatic forces. The continuous fibers can be converted into non-woven fabrics, which may be useful for synthesizing novel membranes due to their high surface-to-volume ratios.

A need exists to fabricate wet spun or electrospun fibers using nanometer scale liquid crystalline viral particle suspensions where the particle composition and function can be easily modified genetically to include binding or nucleating conjugate moieties for inorganic and/or organic materials, while maintaining the fibrous structure end product. If the conjugate materials are inorganic, this provides fabrics with controlled electrical, magnetic, or mechanical properties. If the conjugate particles have one or more binding functions, the fibers/fabrics could be used as filtration detectors for airborne or dissolved analytes. Combinations of material composition and nanoparticle function could be employed for more complex applications of detection or unique flexible devices.

SUMMARY

The invention provides a plurality of methods of fabricating virus-based micro- and nanometer scale fibers that, generally, can be in broad terms a mimic of the spinning process of silk spiders. In some embodiments of the invention, wet spinning and electrospinning were used to fabricate virus- based micro- and nanofibers, respectively. In some embodiments, the resulting fibers showed nematic ordered morphologies due to flow forces. In additional embodiments, the virus was blended with a synthetic carrier polymer, poly(vinyl pyrrolidone) (PVP), to improve its processing ability. The resulting virus blended PVP fibers were continuous and could be formed into non-woven fabrics mats that retain their ability to infect bacterial hosts.

In particular, the present invention provides a method of forming a viral fibrous material comprising a plurality of fibers comprising the steps of providing virus particles and a solvent in a fiber spinning composition, and then fiber spinning the virus particles to form the fibrous material. The spinning can be a wet fiber spinning, an electrospinning, a microfiber spinning, or a nanofiber spinning. The fiber spinning composition can be a lyotropic liquid crystalline composition. The virus particles can be bacteriophage virus particles. The virus particles can form lyotropic liquid crystalline solutions. The virus particles can possess specific binding regions on their particle surface. The virus particle can possess selective binding regions on their surface and can be bound to a conjugate material. The conjugate material can be an organic material, a particulate material, or a nucleated nanoparticulates material. The virus particles can possess genetically engineered expressed peptide sequences for selective binding to a conjugate material. Fiber spinning can be carried out with crosslinking of the viral particles to form cross-linked fiber. After spinning, the fibrous material can be liquid crystalline in the semi-dry or dried, solid state. The material can be birefringent and show the nematic phase. The virus particles can possess genetically engineered expressed peptide sequences for specific binding to or nucleation of conjugate material, wherein the fibrous material comprises virus nucleic acids which can be harvested and amplified.

Moreover, the present invention provides a method of forming a genetically engineered fibrous material comprising a plurality of fibers comprising the step of fiber spinning genetically engineered virus particles to form the fibrous material, wherein the virus particles of the fibrous material are specifically bound to a conjugate material after fiber spinning or are capable of specifically binding to a conjugate material after fiber spinning, and the virus particles of the fibrous material retain the virus structure after fiber spinning. The virus particles can be filamentous virus particles. The virus particles can possess specific binding regions on their surface at one end of the virus particle or along the length of the viral surface. The virus particles can also possess specific nucleation regions on their surface at one end of the virus particle and along the length of the viral surface. The method can further comprise the step of blending the fibrous material with one or more other materials.

The present invention further provides a fibrous material comprising a plurality of fibers, wherein the fibers comprise one or more virus particles which retain a viral structure in the solid state. The fibrous material can further comprise non-viral blending material including polymer blending material, including synthetic polymer blending material. The blending material can be a water-soluble polymeric blending material.

Also, the inventors have discovered a fibrous material comprising a plurality of fibers, wherein the fibers comprise one or more fiber spun, genetically engineered virus particles which retain a viral structure in the fiber state and have specific binding sites for binding to a conjugate material. The particles can be specifically bound to the conjugate material. The particles can be capable of but not specifically bound to the conjugate material. The fibrous material can comprise at least 50 wt. % virus particles. Or, the fibrous material can comprise less than 50 wt. % virus particles. The fibrous material can comprise at least 50 wt. % synthetic polymer material. The fibrous material can comprise at least two different types of virus particles. The fibrous material can comprise at least one water-soluble polymer. The fibrous material can comprise at least one biodegradable polymer. The fibrous material can be redissolved into its viable constituent parts.

The invention further provides a fibrous material comprising aligned, crosslinked, rod-like particles, wherein the particles have a cross sectional diameter of about 5 nm to about 20 nm, and a length of about 60 nm to about 6,000 nm. The length can be about 250 nm to about 1,000 nm. The particles can have an aspect ratio of at least 25:1, at least 75:1, or at least 100:1. The particles can be genetically engineered virus particles and can comprise protein and nucleic acid components.

The present invention further provides a method comprising the step of: infecting a host with a viral material, wherein the viral material is provided from a fibrous material comprising virus particles in fiber form.

The present invention further provides a method of converting virus particles to fiber form in which the virus particles retain their virus structure in the solid state comprising the step of spinning the viral particles into fiber form while controlling concentration, viscosity, and optional use of electric field and blending agent to control the fiber form and retain the virus structure after spinning. The concentration can be controlled so that a liquid crystalline phase can be formed for spinning. The concentration can be sufficiently high during spinning to avoid electrospraying.

The present invention also provides experimental conditions which provide the fibers with useful properties such as, for example, the ability to be specifically bound to the conjugate material after fiber spinning or retain the ability to specifically bind to the conjugate material after fiber spinning, as well as retain the ability to infect a host after fiber spinning. For example, concentrations can be adjusted, viscosity can be adjusted, solvents can be altered or replaced, electric fields can be applied, and use of blending materials can be varied.

In another embodiment, the present invention provides a textile comprising a plurality of fibers, wherein each of the fibers comprises a plurality of virus particles arranged in fiber form.

In another embodiment, the present invention provides a nonwoven fabric comprising a plurality of fibers arranged in a planar sheet, wherein each of the fibers comprises at least one virus particle arranged in fiber form.

In another embodiment, the present invention provides a non-woven material or a woven material comprising fibrous material comprising virus particles. Also provided is a sensor comprising fibrous material comprising virus particles. Also provided is a biomedical device comprising fibrous material comprising virus particles. Also provided is a drug delivery device comprising fibrous material comprising virus particles. The device can have fibrous material which further comprises a conjugate material which is delivered at a controlled rate as the fibrous material dissolves upon insertion into tissues or cells. The present invention also provides an article comprising a plurality of fibers comprising virus particles which are genetically engineered to specifically bind to each other.

In another embodiment, the present invention provides a garment with sensors for detecting at least one stimulus, comprising a garment manufactured using fibers comprising viruses engineered to express one or more amino acid oligomers on the exterior surfaces of the viruses that bind with a specified molecule wherein the binding causes a detectable change in the garment.

Still further, the invention provides a method of forming a viral fibrous material comprising a plurality of fibers comprising the steps of providing virus particles and a solvent in a fiber spinning composition, spinning the virus particles to form the fibrous material, wherein the composition is subjected to a nucleation reaction before spinning or the fibrous material is subjected to a nucleation reaction after spinning to form nanocrystals in the fibrous material.

The present invention provides numerous advantages over the prior art. For example, the present invention provides a method of forming fibers on a micrometer or nanometer scale engineered for specific applications, including a wide variety of different applications ranging from military to biomedical. Genetic engineering can be used to engineer the application at an unprecedented level of structural control ranging down to the nanoscale. In another advantage, the viruses used in making the fibers of the present invention may be engineered to express polypeptides having one or more amino acid oligomers on the exterior surface of the viruses. These amino acid oligomers may serve a variety of functions. For example, the amino acid oligomers may be cell adhesion factors, antibodies, or have specificity for inorganic molecules. Fibers provided by the present invention have a variety of application, including but not limited to, scaffolds for tissue engineering, sensors for detecting environmental toxins, reaction sites for chemical reactions, and filters. For nanofibers, particularly when the fiber diameter is about 100 nm or less, the materials can have exceptionally high levels of specific surface area which enables a high proportion of atoms on the fiber surface. This can provide quantum efficiency, nanoscale effect of unusually high surface energy, surface reactivity, high thermal and electrical conductivity, and high strength.

In sum, virus based micro- and nanofibers can be fabricated using wet-spinning and electrospinning processes. M13 viruses in the wet-spun fibers were aligned parallel to the fiber long axis. Electrospun fibers, composed of fragment of M13 viruses and its subunits, were also fabricated by suspending M13 viruses in HFP. Although the viral structure was partially disrupted, these results indicated that the novel biomaterials could be used to expand the dimension of the engineered viruses into endless fibers which can be used to nucleate useful semiconductor nanofibers or to selectively bind desired materials. Additionally, uniform nanofibers fabricated by blending M13 virus with PVP might provide useful biological functions and highly sensitive catalytic functions in future biomedical applications and biosensors.

DETAILED DESCRIPTION

I. Introduction

Figure 1:
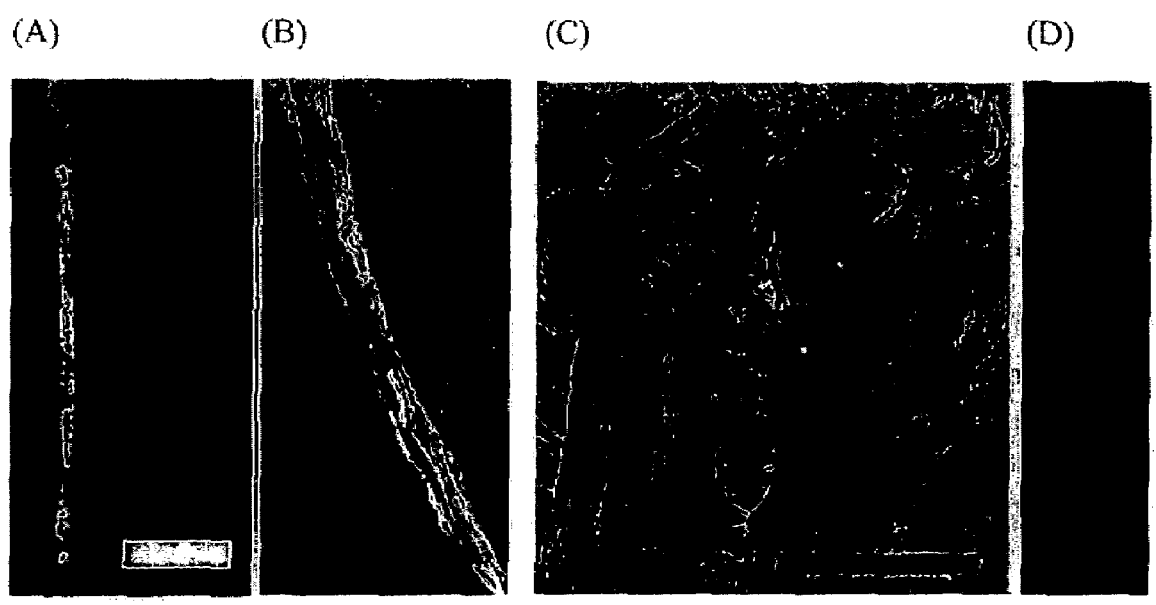
FIG. 1 shows M13 virus fiber fabricated by wet-spinning processes. (A) POM image (scale bars: 100 microns), (B) SEM image (scale bars: 20 microns), and (C) AFM image (scale bars: 20 microns). (D) fluorescence micrographs of virus-phycoerythrin conjugated fibers fabricated by wet-spinning.

In the present invention, virus-based micro- and nanofibers can be fabricated using, for example, wet-spinning and electrospinning processes. The fibers demonstrate that novel biomaterials can be fabricated from a programmed organism to extend the dimension of engineered viruses into fibers useful in, for example, nucleating semiconductor nanofibers or in selectively binding a variety of different types of desired materials. Additionally, in one embodiment, uniform nanofibers can be fabricated by blending nanomaterial-conjugated M13 virus with a water-soluble synthetic polymer, PVP, to provide useful biological functions and highly sensitive catalytic functions. The invention can be used for biomedical applications and biosensors.

In practice of the present invention, reference can be made to the thesis, Lee S.-W., Doctoral Thesis, The University of Texas (Austin), 2003, and in particular to chapter and descriptions focused on fibers, which is incorporated herein by reference in its entirety. In addition, reference can be made to the following papers, including their figures (i) C. E. Flynn et al. *Acta Materiala*, 51, 5867-5880 (2003) entitled "Viruses as vehicles for growth, organization, and assembly of materials." (ii) Seung-Wuk Lee et al., *Nanoletters*, 4, (3), 387-390 2004 entitled "Virus-Based Fabrication of Micro- and Nanofibers Using Electrospinning," the complete disclosures of which are incorporated herein by reference in their entirety. In addition, priority provisional application 60/510,862 filed Oct. 15, 2003 to Belcher et al. is hereby incorporated by reference in its entirety.

In addition, one skilled in the art can also refer to the following patent literature for selection of the virus, genetic engineering methods, and for materials to be used with genetically engineered viruses: phage display libraries and experimental methods for using them in biopanning are further described, for example, in the following U.S. patent publications to Belcher et al.: (1) "Biological Control of Nanoparticle Nucleation, Shape, and Crystal Phase"; 2003/0068900 published Apr. 10, 2003; (2) "Nanoscale Ordering of Hybrid Materials Using Genetically Engineered Mesoscale Virus"; 2003/0073104 published Apr. 17, 2003; (3) "Biological Control of Nanoparticles"; 2003/0113714 published Jun. 19, 2003; (4) "Molecular Recognition of Materials"; 2003/0148380 published Aug. 7, 2003, (5) "Composition, method, and use of bifunctional biomaterials"; 2004/0127640; filed Sep. 4, 2003; (6) "Peptide Mediated Synthesis of Metallic and Magnetic Materials"; Ser. No. 10/665,721, filed Sep. 22, 2003; and (7) "Fabricated Bio-Film Storage Device"; 2004/0171139, filed Sep. 24, 2003, which are each hereby incorporated by reference in their entirety. These references describe a variety of specific binding modifications which can be carried out for binding to conjugate structures, as well as forming the conjugate structures in the presence of the material modified for specific binding. In particular, polypeptide and amino acid oligomeric sequences can be expressed on the surfaces of viral particles, including both at the ends and along the length of the elongated virus particle such as M13 bacteriophage, including pIII and pVIII expressions, as well as pIX, pVII, and pVI expressions, and combinations thereof.

One skilled in the art can also refer to (i) Nam et al., *Nano Lett.*, 2003, 4, 23-27; (ii) provisional application "MULTIFUNCTIONAL BIOMATERIALS AS SCAFFOLDS FOR ELECTRONIC, OPTICAL, MAGNETIC, SEMICONDUCTING, AND BIOTECHNOLOGICAL APPLICATIONS", 60/511,102 filed Oct. 15, 2003 to Belcher et al., and (iii) the regular application to Belcher et al., Ser. No. 10/965,227, "MULTIFUNCTIONAL BIOMATERIALS AS SCAFFOLDS FOR ELECTRONIC, OPTICAL, MAGNETIC, SEMICONDUCTING, AND BIOTECHNOLOGICAL APPLICATIONS", filed on the same day as the present application, which are each incorporated by reference in their entirety, including figures, claims, and working examples.

In addition, the annealing of nanocrystalline nanowires by thermal treatment to form annealed nanowires, and if desired, to remove the underlying viral scaffold is described in, for example, (i) "Peptide Mediated Synthesis of Metallic and Magnetic Materials"; Ser. No. 10/665,721, filed Sep. 22, 2003; (ii) U.S. provisional application to Belcher et al, 60/534,102, filed Jan. 5, 2004, "Inorganic Nanowires."; and (iii) Belcher et al., *Science*, 303, 213 (2004); which are each incorporated by reference in their entirety including figures, claims, and working examples.

"Selection of Peptides with Semiconductor Binding Specificity for Directed Nanocrystal Assembly"; Whaley et al., Nature, Vol. 405, Jun. 8, 2000, pages 665-668, herein incorporated by reference, shows a method of selecting peptides with binding specificity using a combinatorial library. Specifically, the article shows a method of selecting peptides with binding specificity to semiconductor materials using a combinatorial library with about $10^9$ different peptides. The combinatorial library of random peptides, each containing 12 amino acids, were fused to the pIII coat protein of M13 coliphage and exposed to crystalline semiconductor structures. Peptides that bound to the semiconductor materials were eluted, amplified, and re-exposed to the semiconductor materials under more stringent conditions. After the fifth round of selection, the semiconductor specific phages were isolated and sequenced to determine the binding peptide. In this manner, peptides were selected with high binding specificity depending on the crystallographic structure and composition of the semiconductor material. The technique could be readily modified to obtain peptides with a binding specificity for not just semiconductor materials, but a range of both organic and inorganic materials.

References 4-7 noted below are also incorporated herein by reference in their entirety. For example, Lee, S.-W.; Mao, C.; Flynn, C. E., Belcher, A. M., *Science*, (2002) 296, 892-895 describes methods of forming lyotropic and solid state liquid crystalline phases for hybrid viral materials; Lee, S.-W.; Lee, S. K.; Belcher, A. M., *Adv. Mat.* (2003), 15, 689 further describes liquid crystalline behavior for hybrid viral materials; Flynn, E. C., Mao, C.; Hayhurst, A.; Williams, J. L.; Georgiou, G.; Iverson, B.; Belcher A. M., *J. Mater. Chem.*, (2003) 13, 2414 describes nucleation processes to form hybrid viral materials; and Mao, Chuanbin; Flynn, Christine E.; Hayhurst, Andrew; Sweeney, Rozamond; Qi, Jifa; Georgiou, George; Iverson, Brent; Belcher, Angela M, *PNAS*, (2003), 100(12), 6946 also describes hybrid viral materials prepared by nucleation.

II. Virus

In the present invention, a variety of fiber structures can be made from elongated structures. The structures can comprise biomolecules including biomolecular macromolecules and oligomers, including peptide portions and nucleic acid portions. The structures can comprise naturally occurring materials as well as synthetic materials and genetically engineered materials in blended and composite arrangements. In the preferred embodiment, these structures comprise both protein and DNA portions and, more particularly, are viruses.

For example, fibrous material can be formed comprising aligned, crosslinked, rod-like particles as fiber building blocks, wherein the particles have a cross sectional diameter of about 5 nm to about 20 nm, and a length of about 60 nm to about 6,000 nm. More particularly, the length can be about 250 nm to about 1,000 nm.

The virus is not particularly limited so long as fibers can be prepared. In general, virus particles which are long, filamentous structures can be used. See, e.g., *Genetically Engineered Viruses*, Christopher Ring (Ed.), Bios Scientific, 2001. Virus particles which can function as flexible rods can be used.

In one embodiment, virus particles are used which are not genetically engineered. However, in general, desirable properties can be achieved when the virus is genetically engineered. In particular, viruses can be used which have been subjected to biopanning so that the virus particles specifically can recognize and bind to materials which were the object of the biopanning. The viruses can be converted to fiber form with or without the conjugate moiety.

Use of filamentous virus in so called directed evolution or biopanning is further described in the patent literature including, for example, U.S. Pat. Nos. 5,223,409 and 5,571,698 to Ladner et al. ("Directed Evolution of Novel Binding Proteins").

The size and dimensions of the virus particle can be such that the particle is elongated. For example, fibrous viral material can be formed comprising aligned, crosslinked, rod-like particles, wherein the viral particles have a cross sectional diameter of about 5 nm to about 20 nm, and a length of about 60 nm to about 6,000 nm. More particularly, the length can be about 250 nm to about 1,000 nm.

Mixtures of two or more different kinds of viruses can be used. Mixtures of virus particles with non-virus materials can be used.

Virus particle can include both an entire virus and portions of a virus including at least the virus capsid. The term virus can refer to both viruses and phages. Entire viruses can include a nucleic acid genome, a capsid, and may optionally include an envelope. Viruses as described in the present invention may further include both native and heterologous amino acid oligomers, such as cell adhesion factors. The nucleic acid genome may be either a native genome or an engineered genome. "Virus particle" further includes portions of viruses comprising at least the capsid.

In general, a virus particle has a native structure, wherein the peptide and nucleic acid portions of the virus are arranged in particular arrangements, which is sought to be preserved when it is spun into a fiber form. The virus and/or nucleic acids may be replicated after being fabricated into a fiber form. If during fiber formation, viral re-infectivity is lost, information may be still stored, programmed, propagated, and addressable through proteins and engineered nucleic acids, including DNA oligomers, in the viral fiber.

Viruses are preferred which have expressed amino acid oligomer as specific binding sites. Amino acid oligomers can include any sequence of amino acids whether native to a virus or heterologous. Amino acid oligomers may be any length and may include non-amino acid components. Oligomers having about 5 to about 100, and more particularly, about 5 to about 30 amino acid units as specific binding site can be used. Non-amino acid components include, but are not limited to sugars, lipids, drugs, enzymes, or inorganic molecules, including electronic, semiconducting, magnetic, and optical materials.

The fibers of the present invention have varied properties depending on the viruses comprising the fibers and the methods used to manufacture the fibers. For the purpose of this disclosure, fiber refers to generally cylindrical structures that may go by different names, including but not limited to, nanofibers, fibrils, nanofibrils, filaments, or nanofilments. The length, diameter, and aspect ratio (ratio of length over diameter) may vary over a considerable range. Generally, the fibers may be characterized by an aspect ratio of at least 25, at least 50, at least 75, at least 100, or even at least 250 or 500. The diameter of the fibers is typically less than about 20 microns, and more particularly, less than about one micron, including down to about 50 nm, with a minimum diameter of the diameter of the individual virus particles comprising the fibers. The average diameter can be, for example, about 50 nm to about 20 microns, or about 100 nm to about 500 nm. The length of the fibers may vary considerably, but typically will be at least 10 microns and preferably at least 50 microns. Macroscopic fiber spinning with fibrous materials having lengths on the order of mm, cm, and meters are within the invention. These macroscopic fibers can be made up of smaller fibril units as known in the art.

A wide variety of viruses may be used to practice the present invention. The fibers may comprise a plurality of viruses of a single type or a plurality of different types of viruses. Preferably, the virus particles comprising the fibers of the present invention are helical viruses. Examples of helical viruses include, but are not limited to, tobacco mosaic virus (TMV), phage pf1, phage fd1, CTX phage, and phage M13. These viruses are generally rod-shaped and may be rigid or flexible. One of skill in the art may select viruses depending on the intended use and properties of the desired fiber.

Preferably, the viruses of the present invention have been engineered to express one or more peptide sequences including amino acid oligomers on the surface of the viruses. The amino acid oligomers may be native to the virus or heterologous sequences derived from other organisms or engineered to meet specific needs. The expression of the amino acid oligomers may serve a number of functions, including but not limited to, cell adhesion factors, trophic factors, binding sites for organic or inorganic molecules or particles or nucleation sites for organic or inorganic molecules or particles. Expression of amino acid oligomers allows the viruses and fibers comprising the fibers to be engineered to specific applications. For example, the fibers comprising engineered fibers may contain amino acid oligomers that initiate or enhance cell growth for use in tissue engineering applications and bone regeneration. In another example, amino acid oligomers with specificity for a specific inorganic molecule may be expressed to bind or nucleate the inorganic molecule to increase the efficiency of a chemical reaction. In still another example, the expressed amino acid oligomer may bind and detect an organic molecule, such as a biological warfare agent. Such fibers could be incorporated into the clothing of military personnel or first responders as part of a sensor system. Another embodiment is the encryption of information within the genetic code of the viruses. These are only a few examples of the utility of fibers made from engineered viruses, and other applications are readily apparent to one of skill in the art.

A number of prior art references teach the engineering of viruses to express amino acid oligomers and may be used to assist in practicing the present invention. For example, U.S. Pat. No. 5,403,484 by Ladner et al discloses the selection and expression of heterologous binding domains on the surface of viruses. U.S. Pat. No. 5,766,905 by Studier et al discloses a display vector comprising DNA encoding at least a portion of capsid protein followed by a cloning site for insertion of a foreign DNA sequence. The compositions described are useful in producing a virus displaying a protein or peptide of interest. U.S. Pat. No. 5,885,808 by Spooner et al discloses an adenovirus and method of modifying an adenovirus with a modified cell-binding moiety. U.S. Pat. No. 6,261,554 by Valerio et al shows an engineered gene delivery vehicle comprising a gene of interest and a viral capside or envelope carrying a member of a specific binding pair. U.S. Published Patent Application 2001/0019820 by Li shows viruses engineered to express ligands on their surfaces for the detection of molecules, such as polypeptides, cells, receptors, and channel proteins.

III. Conjugate

In the present invention, the virus can be conjugated with a conjugate material before fiber spinning or after fiber spinning.

The conjugate material is not particularly limited. In general, it will be selected for a particular application. The conjugate material can be conjugated to the virus particles by being subjected to viral biopanning against the conjugate material, and then the conjugate material is specifically bound to the virus particle and the fiber formed. Alternatively, fibers can be formed and then the conjugation carried out in, for example, a surface treatment. Conjugate material can be preformed and then bound to the virus or it can be directly formed or nucleated on the virus. The virus can act as a catalyst for formation of or biomineralization of the conjugate material on the virus.

Examples of general types of conjugate materials include inorganic, organic, particulate, nanoparticulate, small molecule, single crystalline, polycrystalline, amorphous, metallic, magnetic, semiconductor, polymeric, block copolymer, functional polymer, conducting polymeric, light-emitting, phosphorescent, organic magnet, chromophore, protein, peptide, nucleic acid, DNA, RNA, oligonucleotide, drugs, enzymes, and fluorescent materials. Conjugate materials are described further, for example, in the patent publications and technical literature to Angela Belcher and co-workers cited in this specification.

The conjugate material can be directly bound to the virus, or can be linked to the virus by an intermediate linking moiety which can both bind to the virus and the conjugate material.

In a preferred embodiment, the conjugate material is a nanomaterial. Examples include semiconductor nanocrystals or quantum dots which have average diameters small enough to provide quantum confinement effects. Average diameters can be about 10 nm or less, or more particularly, about 5 nm or less. Nanowires can also be formed by conjugation of nanocrystalline materials along the length of the virus and annealing the nanocrystalline materials into nanowires. The crystals can be single crystals and can be oriented in the same direction.

IV. Fiber Spinning Including Wet Spinning

Many methods can be used to convert the virus to fiber form, whether alone or with one or more blending materials. The invention encompasses a variety of fibrous structures including microfibers and nanofibers. See, e.g., *Spinning, Extruding, and Processing of Fibers: Recent Advances*, J. S. Robinson, Noyes, 1980; and *Advanced Fiber Spinning Technology*, Toshinari Nakajima (Ed.), Woodhead Pub., 1994.

Spinning generally can be used in fiber production to extrude a solution through an orifice and, if desired, subsequent cross-linking to form longer fibers. Fibers can be spun which have aspect ratios of 50 or more, 100 or more, 500 or more, and 1,000 or more.

Fiber spinning is generally described in *Textbook of Polymer Science*, 3rd Ed., F. Billmeyer, 1984, Chapter 18, pages 486-505, including textile and fabric properties, spinning, fiber after-treatments, and fiber properties, which is hereby incorporated by reference in its entirety. After-treatments include steps taken before weaving including washing, scouring, sizing, lubricating, dying, and property adjustments for control of crease resistance, softness, water repellency, slipping, dimensional stability, shrinkage, and the like. In non-woven fabrics, fibers can be bonded together into flat sheets by heat, pressure, and bonding agents. Finishes can be applied to the fibers. Conventional methods in the art can be used for making non-woven fabrics. Fibers and fiber spinning are also described in the *Concise, Encyclopedia of Polymer Science and Engineering*, J. Kroschwitz, Ed. 1990, "Fibers", pages 374-395.

The present invention teaches methods of forming a fiber comprising the steps of providing a solution or suspension comprising a plurality of virus particles and a solvent and spinning the solution or suspension. The virus particles in solution may be selected based on a variety of criteria as described previously. The solvent selected will depend on the choice of virus particle. Often, the solvent will simply be water with buffering agents, such as TRIS-HCl. The solution may include additional components. Such additional components include, but are not limited to, viscosity modifying agents, ionic strength modifying agents, aligning agents, and buffering agents. Spinning processes are well-known in the fiber manufacturing art and include wet spinning, dry spinning, and electrospinning. Spinning processes can be selected based on the specific application of the resulting fibers. In general, compositions for spinning are selected to avoid components in amounts sufficiently large to interfere with the fiber forming process.

In a preferred embodiment of the present invention, the solution comprising viruses and a solvent will be a liquid crystal solution including lyotropic solutions. Fibers formed from liquid crystal solutions have been shown to have desirable physical properties, such as high strength and uniformity. "Model Study of the Spinning of Thermotropic Liquid Crystalline Polymers: Fiber Performance predictions and Bounds on Throughput"; Forest et al., *Advances in Polymer Technology*, vol. 18, No. 4, pages 314-35 provides background information on the spinning of liquid crystalline solutions and is herein incorporated by reference.

A number of viruses have been shown to form liquid crystal phases in solution. Typically, the viruses are generally rod-shaped and may be rigid or flexible. The structure can have a portion which is rigid, and the rigid portions are connected by flexible portions, so that the virus particle overall is semirigid. Examples of viruses forming liquid crystal phases in solution include, but are not limited to, tobacco mosaic virus (TMV), phage pf1, phage fd, and phage M13. The phases of the liquid crystalline viruses may be altered by changing the solution concentrations, ionic strength of the solution, or altering an external magnetic field or flow velocity. Methods of changing the phase will be readily apparent to one of skill in the art. The following documents give background information generally regarding liquid crystal virus solutions and phase adjustments that may be used to practice the present invention and are herein incorporated by reference: (1) "Smectic Phase in a Colloidal Suspension of Semiflexible Virus Particles"; Dogic et al., *Physical Review Letters*, Vol. 78, No. 12, pages 2417-20 and "Ordering of Quantum Dots Using Genetically Engineered Viruses"; Lee et al., *Science*, Vol. 296, pages 892-95. It is not necessary for the solutions containing viruses to be in a particular phase in order to spin fibers.

The spinning processes that may be used in the present invention are well-known within the art and include, but are not limited to, dry spinning, wet spinning, and electrospinning. In dry spinning, the solution comprising virus particles and a solvent is passed through a spinneret into a zone where the solvent is quickly evaporated leaving fibers that may be wound. Fibers produced by wet spinning are formed by passing the solution comprising virus particles and solvent through a spinneret into a nonsolvent that coagulates the virus particles. A chemical reaction may be involved in forming fibers using this process. Crosslinking can occur. The specific parameters of the spinning processes may be readily determined by one of ordinary skill in the art.

Preferred embodiments include wet fiber spinning, electrofiber spinning, and lyotropic liquid crystalline fiber spinning.

Wet spinning is known in the art including use of wet spinning to form fibrous, microfibrous, and nanofibrous materials.

The solvents and suspension agents used are not particularly limited. The wet spinning can be carried out, for example, with use of aqueous solutions and suspensions. Concentrations can be used so that lyotropic liquid crystalline solutions can be formed including—smectic and nematic solutions. Concentrations can be, for example, about 10 to about 1,000 mg/mL, and more particularly, about 50 mg/ML to about 250 mg/mL. pH can be adjusted as needed.

Capillary tubes can be used for extrusion. The size can be, for example, about 1 micron to about 100 microns, and more particularly, about 5 microns to about 50 microns.

Crosslinking of the fibrous structures can be carried out. The crosslinking agent is not particularly limited but can be electrophilic agents, including carbonyl moieties such as, for example, glutaraldehyde solutions. Concentration of the crosslinking agent can be, for example, about 10% to about 60%, and more particularly, about 25% to about 50%.

When microfibers are made, the diameters of the microfibers can be, for example, about one micron to about 100 microns, and more particularly, about 5 microns to about 50 microns, and more particularly about 10 microns to about 20 microns.

Experimental variables such as crosslinking agent, concentration, extrusion rate, and size of capillary can be adjusted to provide the desired fibers.

Wet spinning is illustrated in FIG. 4.

V. Electrospinning

Electrospinning of fibers in known in the art and is described in the patent literature at, for example, U.S. Pat. Nos. 6,106,913 and 6,308,509 to Scandino et al. ("Fibrous Structures Containing Nanofibrils and Other Textile Fibers"); U.S. Pat. No. 6,110,590 to Zarkoob et al. ("Nanofibers and a Process for Making the Same"); U.S. Pat. Nos. 6,382,526 and 6,520,425 to Reneker et al. ("Process and Apparatus for the Production of Nanofibers"); and U.S. Pat. No. 6,616,435 to Lee et al. ("Apparatus of Polymer Web by Electrospinning Process"). In addition, the following references including background material on electrospinning techniques may be used to practice the present invention and are herein incorporated by reference: (1) "Nanostructured Fibers via Electrospinning"; Bognitzki et al., *Adv. Mater.*, Vol. 13, No. 70, pages 70-XX (2001) and "Preparation of Fibers with Nanoscaled Morphologies: Electrospinning of Polymer Blends"; Bognitzki et al., *Polym. Eng. Sci.*, in press (2001).

Figure 4:
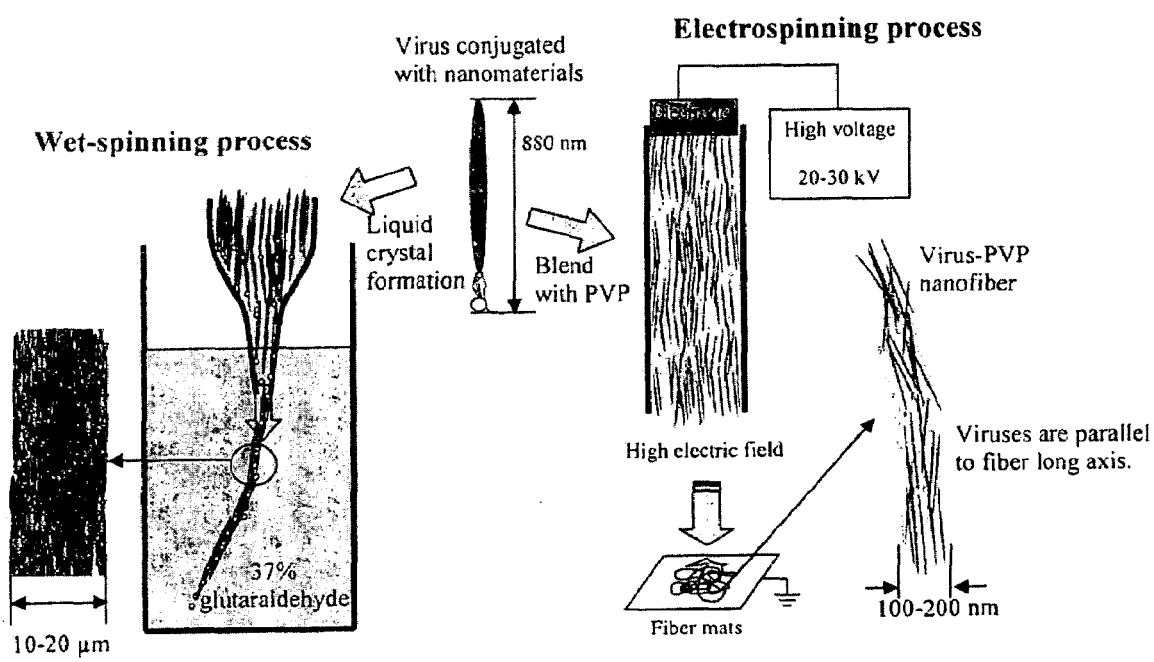
FIG. 4 shows a schematic diagram illustrating virus fiber fabrication process using wet-spinning and electrospinning.
Figure 5:
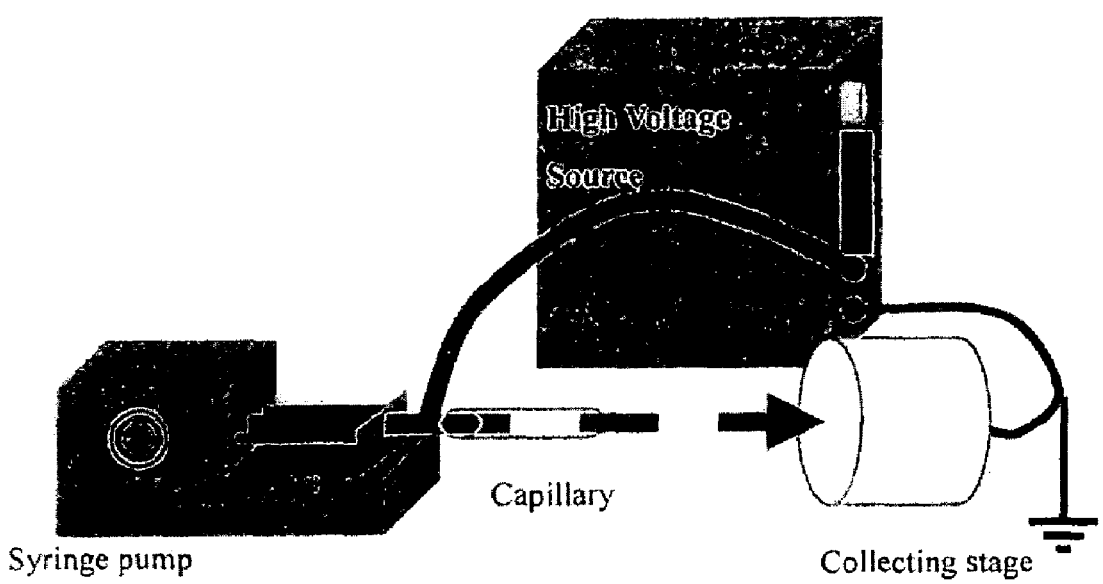
FIG. 5 shows schematic illustration of electrospinning apparatus (A) and its photograph (B).
Figure 5:
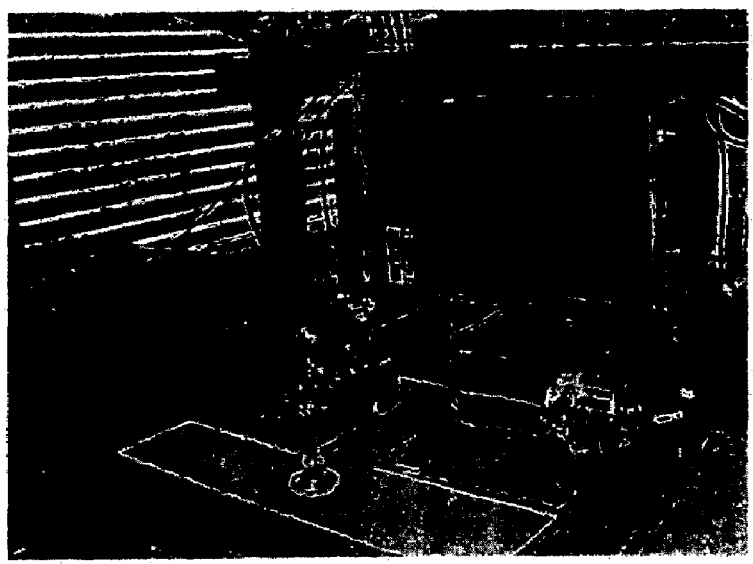

Electrospinning is also illustrated in FIGS. 4 and 5 (including photograph of apparatus).

Volatile organic solvents can be used for electrospinning. Conditions for suspending the virus in the solvent can be adjusted to provide the desired fibers. Solvents are preferred which provide a homogeneous virus suspension. Also, the solvent should allow the virus to retain its ability to infect. Concentrations can be used so that lyotropic liquid crystalline solutions can be formed including smectic and nematic solutions. Concentrations can be, for example, about 10 to about 1,000 mg/mL, and more particularly, about 50 mg/ML to about 250 mg/mL.

Spinning conditions can be also adjusted including, for example, pump feed rate, applied potential, collection plate, and distance between capillary and collector plate. Other parameters include polymer and viral concentration, molecular weight, solution viscosity, Berry Number, boiling point, distance, voltage, and orifice diameter.

VI. Blending Material

The fiber spinning of the virus particles can be carried out with a non-viral blending material for the virus particles, including a polymeric blending material. This can also be a carrier. The blending material can be a synthetic polymer blending material. It can be a water-soluble polymeric blending material. It can be, for example, a vinyl polymer which has polar side groups which can, if desired, provide for water solubility. Examples include polycarbonate, DNA, silk, aramid, polystyrene, polybutadiene, nylon, polyester, PLGA, PLAGA, polyacrylonitrile, polyaniline and other conjugated polymers, and PVDF. A preferred example is PVP. Polymers can be selected which are glassy at room temperature, having a glass transition temperature above 25° C. The molecular weight of the blending material can be selected to be high enough to provide for good fiber properties. For example, molecular weight (Mn) of at least 100,000, or of at least 500,000, or of at least 1,000,000 can be selected.

This infection ability of the M13 virus fibers blended with PVP can be useful in biomedical applications and tissue engineering. One skilled in the art can tailor the infectability to the level desired for that application. In some applications, infectability may be undesired. In some applications, mere storage of the virus, including information stored in the DNA, may be useful without need for the infectability. In other applications, the high levels of infectability may be an important parameter.

The relative concentrations of the virus and the blending material can be adjusted to provide the desired fibral structures. In some embodiments, the blending material is more than 50 wt. % of the fiber, whereas in other embodiments, the blending material is less than 50 wt. % of the fiber.

The fiber diameter can be, for example, about 10 nm to about 1,000 nm, or more particularly, about 25 nm to about 500 nm, and more particularly, about 50 nm to about 250 nm.

Fibers can be further annealed and oriented as desired.

VII. Applications

The fibers can be arranged into desired shapes using masks and patterning. Fiber processing methods can be used including yarn processing.

Applications of the invention are many and include

1) Diagnostics (medical or environmental): filter material that is optimized for aqueous samples (because viruses are intrinsically water loving) that contain specific binding sites useful in flow through diagnostic assays (e.g. sandwich assays Ab-Ag-Ag-label, or competition assays where a labeled ligand is displaced). Flow through could be in air. Subsequent labeling could occur in liquid.

2) Diagnostic applications in (1) above can be extended by using multiple virus types for multiple analyte tests, thus producing a test "cocktail" in one membrane material.

3) Bioreactors (therapeutics or other products): fiber meshes or fiber bundles may be used in flow-thru bioreactors where virus components are designed to bind to certain cells and/or contact cells with stimulating agents (e.g. cytokines), Viral conjugate components or viral crosslinking may be designed to release cells or stimulate cells only after a chemical change is made in the flowing media.

4) Non-woven fabrics comprising fibers or fibrous materials with specific optical, electrical, or magnetic properties that are incorporated into textiles as sensors, detectors, and monitors. Military applications can be carried out using soldier gear and uniforms which have the viral fibers.

5) membranes 6) sensors

Figure 6:
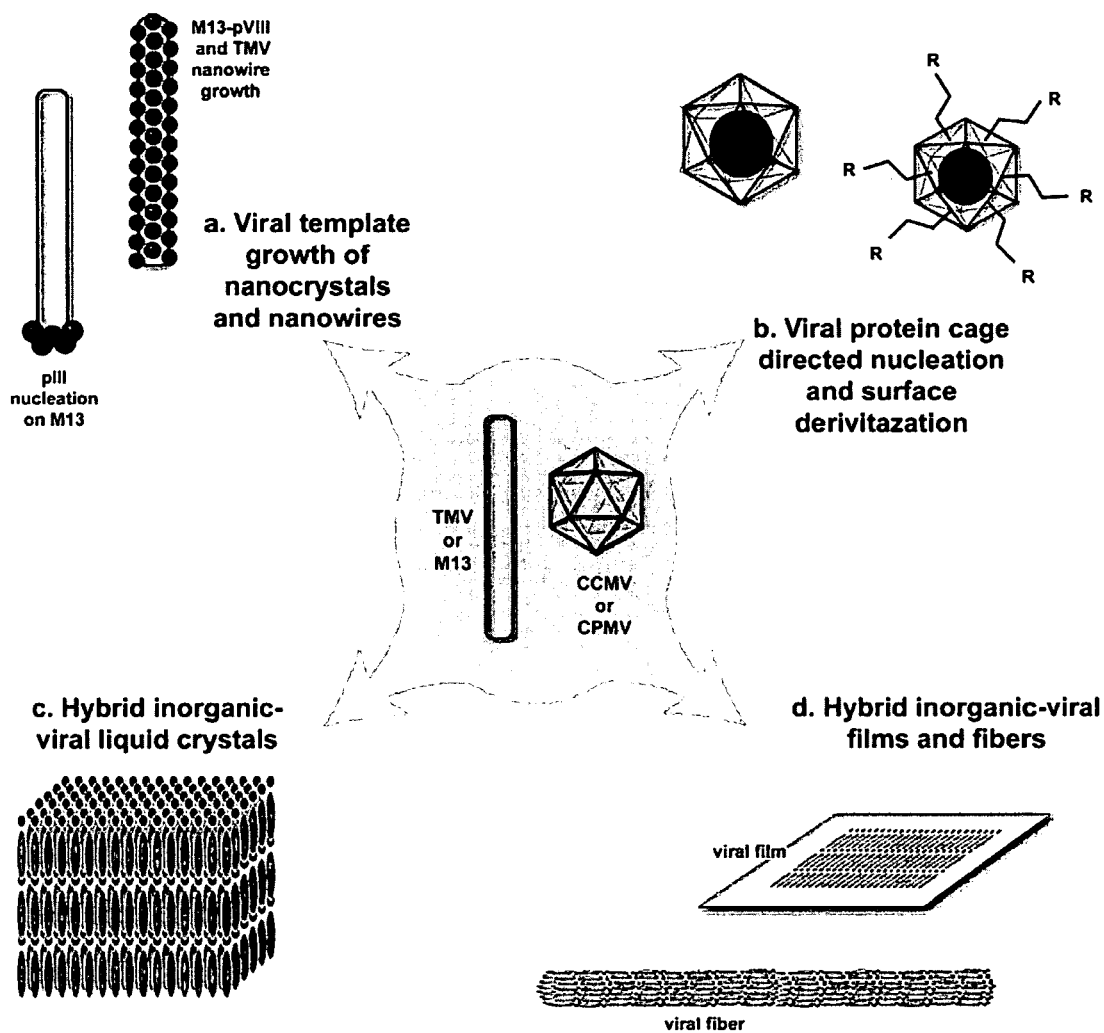
FIG. 6 illustrates hybrid inorganic-viral fibers and films (lower right) as well as other viral-related structures.

Viral fibers are further illustrated in FIG. 6, as well as film structures. Other viral structures useful in many applications are shown (see Belcher patent publications and other paper publications cited herein).

If desired, the fibers can be heat treated and annealed. If desired, organic aspects of the fibers can be removed by thermal treatments at high enough temperatures so that the organic component is "burned off" to leave an inorganic conjugate component, such as a nanowire, which is stable to the high temperatures. In addition, fibers can be modified and genetically engineered so that they can recognize and couple to each other at their ends, or along the sides.

The fibers can be attached to pre-patterned surfaces to form patterns of fibers on the surface and can be deposited in patterned arrangements on surfaces.

Viral fibers can be blended with non-viral fibers.

WORKING EXAMPLES

The invention is further described with use of the following non-limiting working examples.

A. Virus

Anti-streptavidin M13 bacteriophage possessing an engineered peptide sequence, N'-TRP ASP PRO TYR SER HIS LEU LEU GLN HIS PRO GLN-C' (SEQ ID NO.:1), in its pIII coat protein (virus) was used as a basic building block to fabricate the micro- and nanoscale fibers. The virus was selected from the PhD-12 phage display library (New England Biolabs, Inc. Beverly, Mass.) for affinity to streptavidin (5). The virus was amplified and purified according to phage library manufacturer instructions and suspended in tris buffered saline (TBS; 50 mM Tis, 150 mM NaCl, pH 7.5).

B. Conjugate Material.

The bacteriophage was used with or without conjugation with R-phycoerythrin (eBioscience, CA) previously reported [5]. Conjugation was at the pIII subunit.

C. Wet Spinning

The M13 virus suspension (~100 mg/ml) extruded through ~20 um capillary tube into 37.3% aqueous glutaraldehyde solution, were cross-linked and formed microfibers. The fibers were taken and dried in the air. Polarized optical microscopy image (FIG. 1A) taken using Olympus IX51 polarized optical microscope (POM; Olympus, Japan) under the crossed polars exhibited birefringent, which indicates liquid crystalline ordered structures of the fibers. SEM images taken using a JEOL 6320 FEGSEM field emission scanning electron microscope (FE-SEM; JEOL, Japan) (FIG. 1B) of the fibers showed that the fibers had 10-20 micrometer in diameter and were composed of several bundle-like fibers which were propagated to fiber long axis. Parallel orientation of the individual stand of virus building block was observed by AFM. AFM image (FIG. 1C) showed close-packed M13 virus of which long axis was parallel to the long axis of the fibers. Although smectic suspension was spun to fabricate the virus fibers, smectic layered structures were not observed from POM and AFM. Due to flowing field, smectic ordered structure in the suspension was disrupted and smectic to nematic transitions occurred. Because the suspension was immediately exposed to cross-linking solution after releasing from the capillary, the nematic ordered viruses were cross-linked each other and formed nematic ordered fibers. Florescent viral microfibers were fabricated by spinning fibers after conjugation of virus and R-phycoerythrin (eBioscience, CA) covalently conjugated with streptavidin [5]. Uniform fluorescent light (FIG. 1D) throughout the fibers supported the nematic ordered structures observed in POM and AFM which did not have positional ordered structures.

Figure 7:
FIG. 7 provides characterization of wet spun virus fibers. (A) polarized optical microscope image (scale bar: 100 microns) (B-D) SEM images (scale bars: 100 microns (B), 20 microns (C), and (E) surface morphology of the fiber (scale bar: one micron).
Figure 7:
Figure 7:
Figure 7:
Figure 7:
Figure 8:
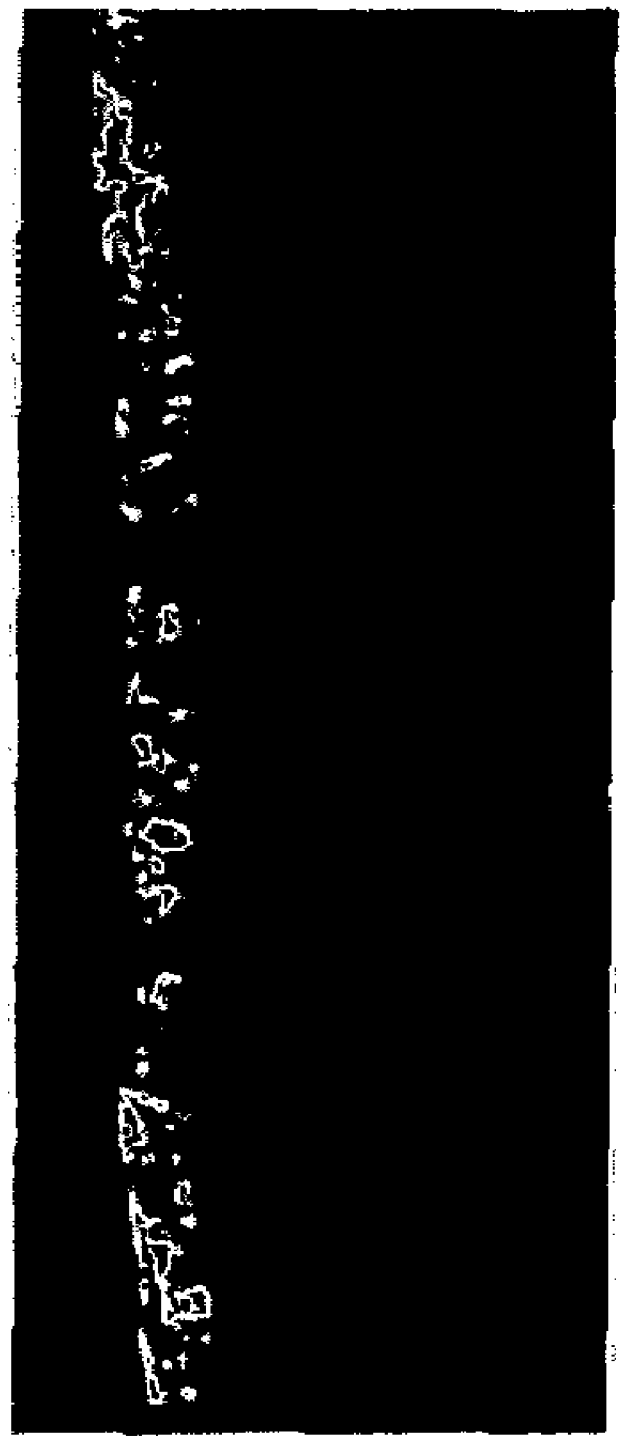
FIG. 8 provides polarized optical micrograph (left) and fluorescence micrograph (right) of wet-spun virus conjugated with R-phycoerythrin fibers.

Wet spun fibers are further shown in FIGS. 7 and 8.

D. Electrospinning

Figure 2:
FIG. 2 shows (A) POM image of electrospun virus-only fibers, (B) SEM image of electrospun virus-only fibers (scale bars: 5 microns).
Figure 2:
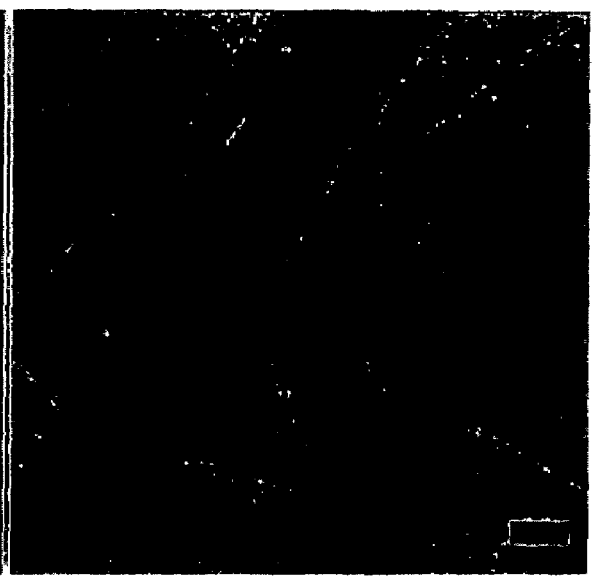

Aqueous M13 virus suspension could not be electrospun but electro-sprayed because the suspension exhibited too low viscosity to be spun. However, M13 viruses suspended in a volatile organic solvent could be spun using electrospinning. Various organic solvents were tested for the possibility as a spinning solvent. However, most of the electrospinning solvents tested, such as methanol, ethanol, DMF, acetone and trifluoroethanol, formed slurry-like aggregation when they were added to virus pellets and suspensions. 1,1,1,3,3,3,hexafluoro-2-propanol (HFP; Alpha Aeser, MA) was the best solvent to form homogenous virus suspension when the virus pellets were dissolved. In order to fabricate nanofibers, capillary tubes (20 ul volume, ~0.5 mm in diameter, 6.5 cm long, Drummond Scientific Co., PA) were filled with virus suspension (~92 mg/ml in HFP), and a graphite rod (0.5 mm in diameter) was inserted into one end of the capillary tube by a syringe pump (Harvard Apparatus, Inc., MA) at a feeding rate of 3-6 ul/min. A 20-30 kV potential was applied by a high voltage source across air (Glassman High Voltage, NJ). Electrospun fibers were collected onto metal plates (10 cm in diameter) grounded and covered by aluminum foil. Distance between capillary and collector was 10-15 centimeters. Polarized optical microscopy image (FIG. 2A) verified that these continuous electrospun fibers were highly birefringent under the cross polars, indicating that there were highly crystalline ordered structures in the fibers. Relatively broad distribution of diameter was observed ranging from a few micrometers to tens of nanometers in diameter. SEM image (FIG. 2B). shows that most of the fibers have branched shaped separated from larger fiber bundles to smaller fibers. Due to the toxicity of HFP to the M13 virus, infectability of M13 virus in HFP solution was dramatically decreased and showed no infectability. Because intact virus structures were rarely observed from the TEM observation, virus fibers spun using HFP could be composed of the fragment of virus and dissembled subunits.

Figure 9:
FIG. 9 provides optical micrograph of electrospun virus fibers (A) and its corresponding polarized optical micrograph of area drawn in dotted box (A), scale bar (100 microns).
Figure 9:
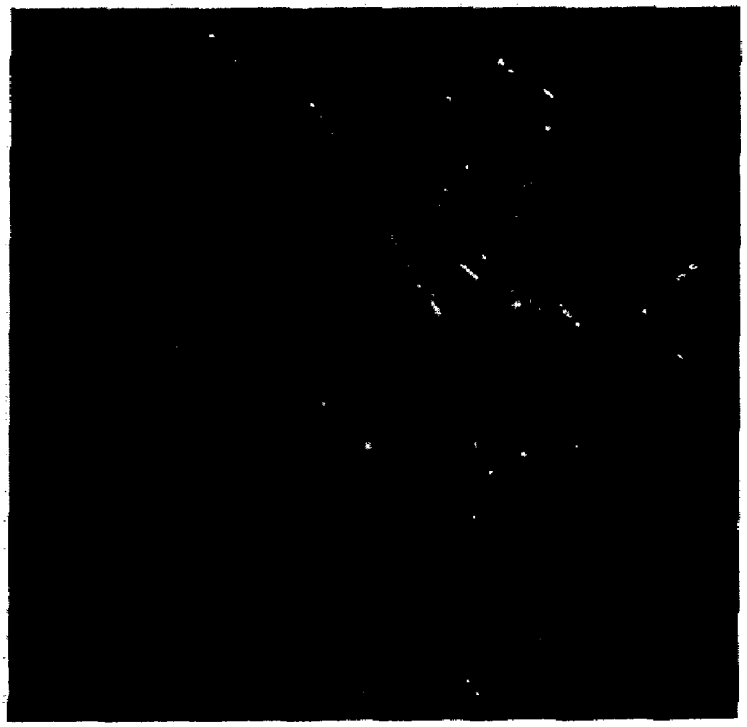
Figure 10:
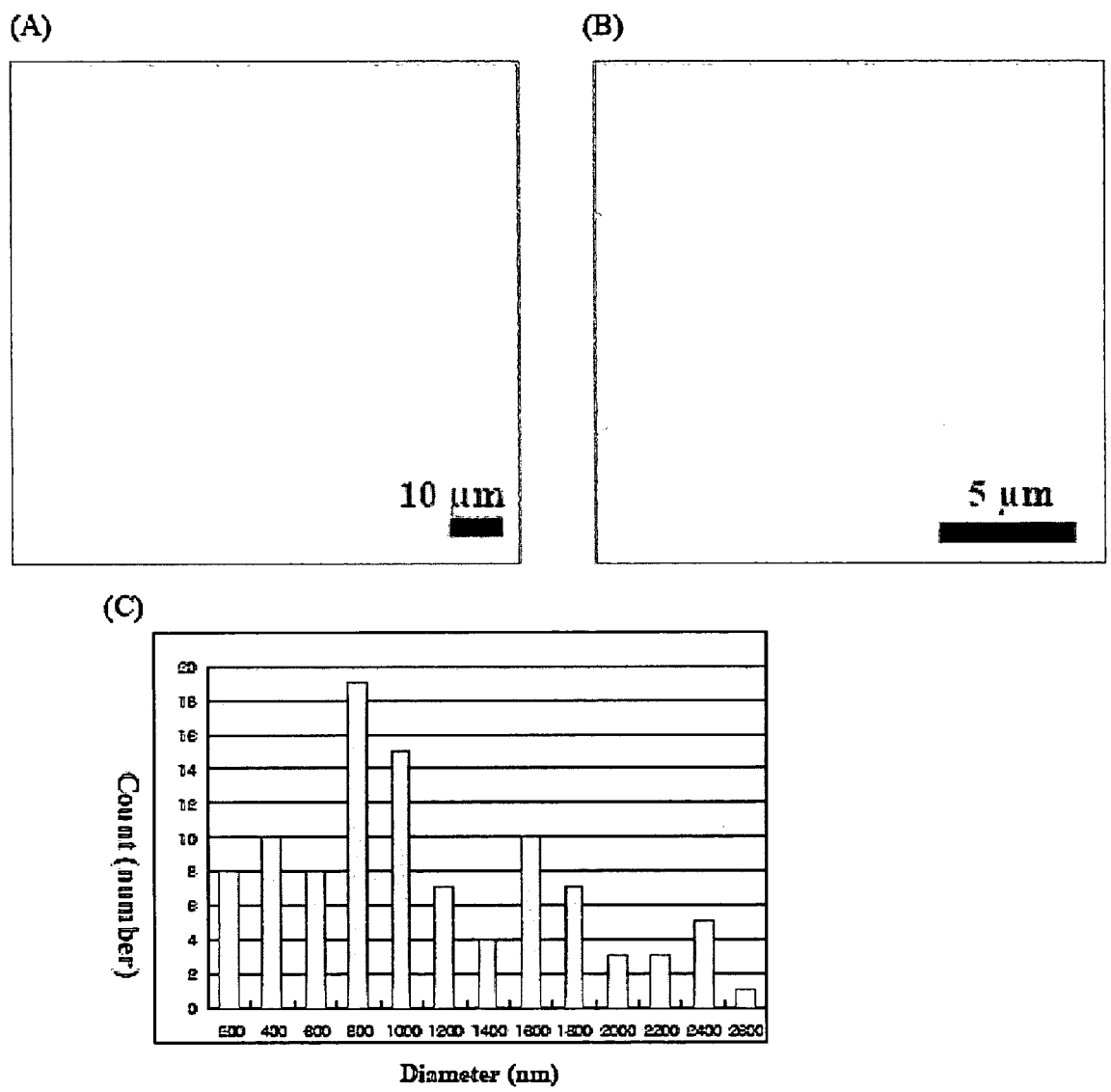
FIG. 10 provides SEM ranges of electrospun virus fibers and distribution of the diameter measured in SEM (scale bars: (A) 10 microns, and (B) 5 microns.

Electrospun fibers are further shown in FIGS. 9 and 10.

E. Electrospinning with Blending Material

Figure 3:
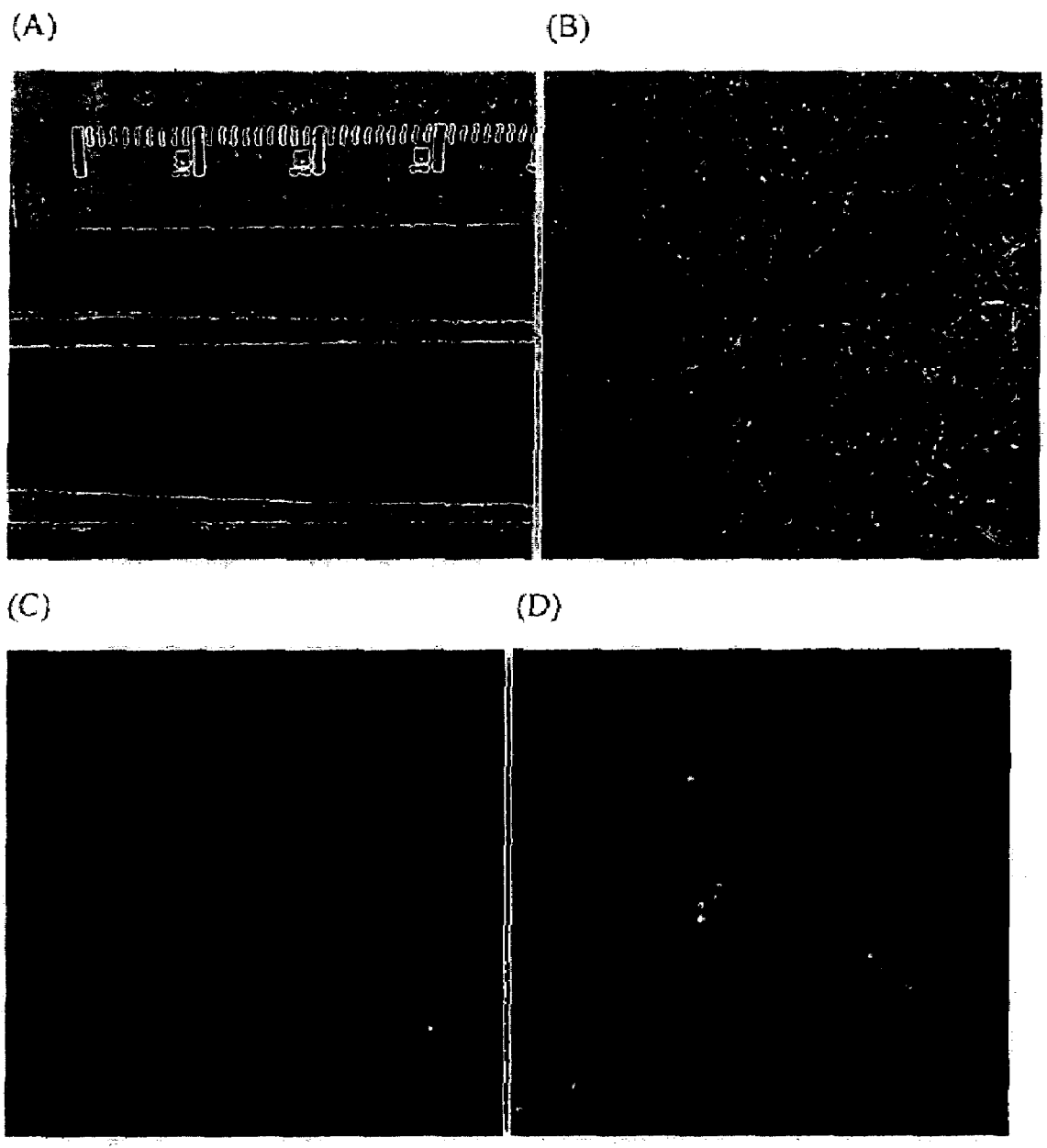
FIG. 3 shows electrospun fiber of M13 virus blended with PVP. (A) Photograph of non-woven fiber spun through the mask inscribed word "NANO", (B) SEM image (scale bar: 1 micron), (C) POM image, (D) fluorescence micrographs of PVP blended with virus-phycoerythrin fibers fabricated by electrospinning.

In order to improve processing ability and preserve the intact viral structure and infecting ability, M13 virus suspension was blended with highly water soluble polymer, polyvinyl 2-pyrolidone (PVP; M.W.: 1,300,000; (Alfa Aesar, MA). The suspensions blended in ratio of 1:1, 1:2, 1:3 and 1:4 between virus suspension in TBS (~100 mg/ml) and PVP solution (25%, (w/w)) in water. Due to the low viscosity and high surface tension of the aqueous suspensions, 1:1 and 1:2 suspensions were not electrospun but deposited droplets of virus-PVP suspension. The 1:3 suspension was sporadically spun and formed bead and string type fibers, which is normally observed in low viscous or concentration solutions in electrospinning process [29-31]. However, there were still many electrosprayed droplets observed. Continuous M13 virus blended PVP fibers were fabricated from the 1:4 suspension. Photographs of electrospun fibers (FIG. 3A) showed that electrospun fibers could be transformed to any shape of non-woven fabrics. A mask was made from simple paper cut-outs placed over a glass substrate on the collector plate. SEM image showed that the resulting fibers were continuous and homogeneous round rope shapes (FIG. 3B). Due to the lack of driving force for the orientation of the fibers, such as rotating mandrels [32,33] or a conducting-gap mounted collector [26], no preferred orientation of the fibers was observed. Distribution of the diameter was relatively narrow although a few micrometers were, still observed. Most of the fibers had diameter ranging 100-200 nanometers. The electrospun fibers observed using polarized optical microscope exhibited nematic-like birefringent (FIG. 3C). The fibers showed maximum brightness when the fibers were oriented ~45 degrees to the cross polars and extinct when the fibers were oriented to parallel with cross polars. When the viruses conjugated with R-phycoerythrin using streptavidin linker, fluorescence images could be observed using fluorescence microscope (FIG. 3D). After dissolving the electrospun fibers in 3 ml of tris-buffered saline (pH: 7.5), the suspension was taken to test infecting ability of the M13 virus. The resuspended virus suspension showed that the virus still active to infect the bacterial host.

Figure 11:
FIG. 11 provides photograph of electrospun fibers of virus blended with PVP, which showed the non-woven fibers could be transformed into any shape.
Figure 12:
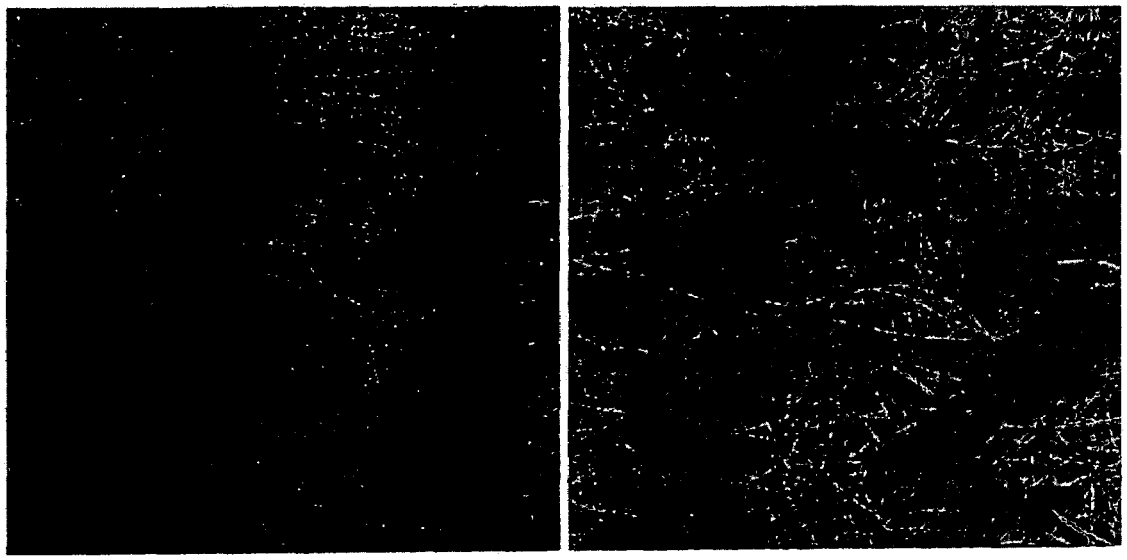
FIG. 12 provides series of SEM images of virus blended with PVP and their diameter distribution (D) measured in SEM, (scale bars (A), (B) 10 microns and (C) one micron).
Figure 12:
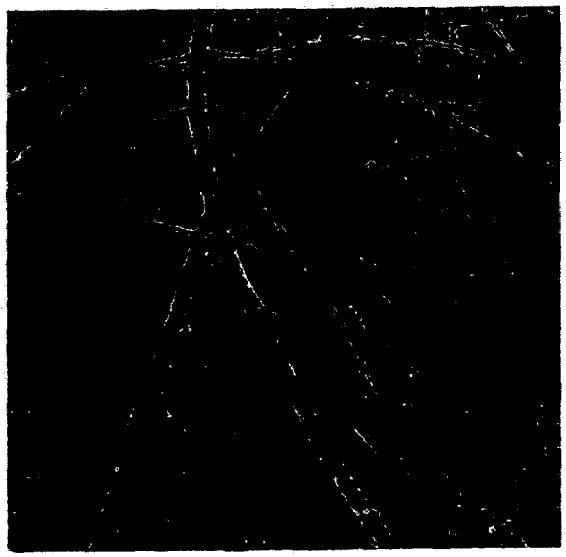
Figure 12:
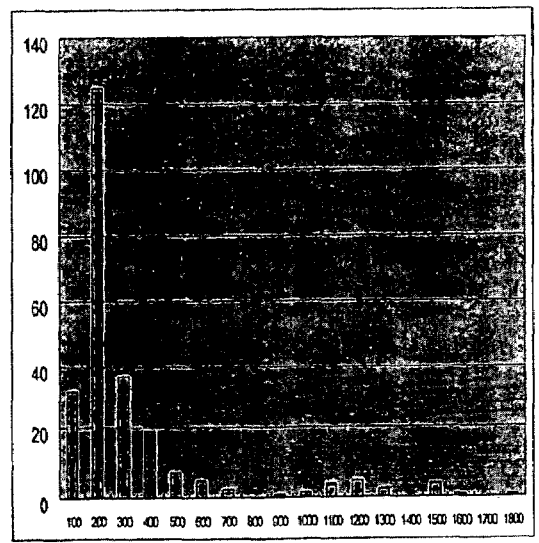
Figure 13:
FIG. 13 provides optical micrographs of PVP blended anti-streptavidin virus conjugated with phycoerythrin. Fluorescence micrograph of virus conjugated with phycoerythrin blended PVP (A) and a polarized optical micrographs of virus blended with PVP (B).
Figure 13:

FIGS. 11-13 further show data from the PVP viral fiber system.

The non-woven fibers can be deposited in higher concentrations in order to synthesize self-supporting non-woven fabrics. Substrates used during the deposition of the non-woven fiber fabrics can be further optimized to further induce self-supporting and oriented systems.

One skilled in the art can further practice the present invention by reference to the following references, which are hereby incorporated by reference in their entirety.

REFERENCES

1. Belcher, A. M. et al. *Nature* 381, 56-58 (1996).
2. Mann, S. *Biomimetic Materials Chemistry;* VCH: New York, 1996.
3. Whaley, S. R., English, D. S., Hu, E. L. Barbara, P. F. Belcher, A. M. *Nature* 2000, 405, 665-668.
4. Lee, S.-W.; Mao, C.; Flynn, C. E., Belcher, A. M., *Science,* (2002) 296, 892-895.
5. Lee, S.-W.; Lee, S. K.; Belcher, A. M., *Adv. Mat.* (2003), 15, 689
6. Flynn, E. C., Mao, C.; Hayhurst, A.; Williams, J. L.; Georgiou, G.; Iverson, B.; Belcher A. M., *J. Mater. Chem.,* (2003) 13, 2414.
7. Mao, Chuanbin; Flynn, Christine E.; Hayhurst, Andrew; Sweeney, Rozamond; Qi, Jifa; Georgiou, George; Iverson, Brent; Belcher, Angela M, *PNAS,* (2003), 100(12), 6946.
8. Douglas, T., Young, M. *Nature* 1998, 393, 152-155.
9. Alivisatos A. P. et al., *Nature* 381, 56-58 (1996).

10. Mirkin C. A., Letsinger R. L., Mucic R. C., Storhoff J. J., *Nature* 382, 607-609 (1996).
11. Ball, P. *Nature* 2001, 413, 667-668.
12. Seeman, N. C. *Nature* 2003, 421, 427-431.
13. Brown, S. *Nature Biotechnol.* 1997, 15, 269-272.
14. Nygaard, S., Wendelbo, R., Brown, S. *Adv. Mat.* 2002, 14, 1853-1856.
15. Vollrath, F., Knight, D. P., *Nature*, (2001) 410, 541-548.
16. Hayashi, C.; Lewis R. V., *Science*, (2002) 287, 1477-1479.
17. Hayashi, C.; Lewis R. V., *J. Mol. Biol.*, (1998) 275, 773-784.
18. Valluzzi, R.; Winkker, S.; Wilson, D.; Kaplan, D. L; *Phil. Trans. R. Soc. Lond. B* (2002) 357, 165-167.
19. Li, L. S., Alivisatos, A. P., *Advanced Materials* (2003) 15 (5): 408-411.
20. Yao, Z., Henk, Postma W. C., Balents L., Dekker C., *Nature*, 402, 273-276.
21. Rueckes, T., Kim K., Joselevich, E., Tseng G. Y., Cheung, C. L., and Lieber, C. M., *Science* 289, 94-97 (2000).
22. Bergshoef., M. M., Vancso, G. J., *Advanced Materials*, (1999), 11, 1362-1365.
23. Jin, H., Fridrikh, S. V., Rutledge, G. C., Kaplan, D. L, *Biomacromolecules* (2002) 3, 1233-1239.
24. Hohman, M. M., Shin, M., Rutledge, G., Brenner, M. P. *Physics of Fluids*, (2001), 13, 2201-2220.
25. Li, D., Xia, Y., *Nano Letters*, (2003) 3, 555-560.
26. Li, D., Wang, Y., Xia, Y., *Nano Letters*, (2003) 3, 1167-1171.
27. Taylor, G., *Proc. Roy. Soc. Lond. A.* (1969), 313, 453-475.
28. Doshi, J.; Reneker, D. H.; *J. of Electrostatics* 1995, 35, 151-160.
29. Megelski, S., Stephens, J. S., Chase, D. B., Rabolt, J. F., *Macromolecules*, (2002), 35, 8456-8466.
30. Huang, L., McMillan, R. A., Apkarian, R. P., Rourdeyhimi, B., Conticello, V., P., Chaikof, E. L., *Macromolecules* (2000), 33, 2989-2997.
31. Wang, X., Drew, C., Lee, S., Senecal, K. J., Kumar, J., Samuelson, L. A., *Nano Letters*, (2002), 2, 1273-1275.
32. Matthews, J. A.; Wnek, G. E.; Simpson, D. G.; Bowlin, G. L. *Biomacromolecules* 2002, 3, 232-238.
33. Wnek, G. E.; Carr, M. E.; Simpson, D. G.; Bowlin, G. L. *Nano Letters*, 2003; 3(2); 213-216.
34. Dogic, Z.; Fraden, S. *Phys. Rev. Lett.* (1997), 78, 2417.

What is claimed is:

1. A method of forming a viral fibrous material comprising a plurality of fibers and a non-viral blending material comprising providing virus particles, a non-viral blending material, and a solvent in a fiber spinning composition, and then spinning the virus particles to form the fibrous material.

2. The method according to claim 1, wherein the spinning is an electrospinning.

3. The method according to claim 1, wherein the virus particles are filamentous virus particles.

4. The method according to claim 1, wherein the virus particles possess selective binding regions on their surface and are bound to a conjugate material.

5. The method according to claim 4, wherein the conjugate material is an inorganic or an organic material.

6. The method according to claim 1, wherein the fiber spinning is carried out with crosslinking of the viral particles to form cross-linked fiber.

7. The method according to claim 1, wherein after spinning the fibrous material is liquid crystalline.

8. A method of forming a genetically engineered fibrous material comprising a plurality of fibers and a non-viral blending material comprising the step of fiber spinning genetically engineered virus particles with a non-viral blending material to form the fibrous material, wherein the virus particles of the fibrous material are specifically bound to a conjugate material after fiber spinning or are capable of specifically binding to a conjugate material after fiber spinning, and the virus particles of the fibrous material retain the virus structure after fiber spinning.

9. A fibrous material comprising a plurality of fibers, wherein the fibers comprise one or more fiber spun, genetically engineered virus particles which retain a viral structure in the fiber state and have specific binding sites for binding to a conjugate material, wherein the virus particles comprise expressed oligopeptide sequences which provide the specific binding.

10. The fibrous material according to claim 9, wherein the conjugate material is a semiconductor material, a magnetic material, or a metallic material.

11. The fibrous material according to claim 9, wherein the conjugate material is a crystalline material.

12. The fibrous material according to claim 9, wherein the conjugate material is a drug or enzyme.

---

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Trp Asp Pro Tyr Ser His Leu Leu Gln His Pro Gln
1               5                   10

13. The fibrous material according to claim 9, wherein the virus particles have specific binding sites at their ends, and along their lengths.

14. The fibrous materials according to claim 9, wherein the fibrous material further comprises metallic, ceramic, or glassy material.

15. The fibrous materials according to claim 9, wherein the fibrous material further comprises polymeric material.

16. The fibrous material according to claim 9, wherein the fibrous material comprises at least two different types of virus particles.

17. The fibrous material according to claim 9, wherein the virus particles are filamentous virus particles and the fibrous material further comprises a blending material.

18. The fibrous material according to claim 17, wherein the fibrous material can be redissolved into its viable constituent parts.

19. A method comprising the step of:
   infecting a host with a viral material, wherein the viral material is provided from a fibrous material comprising virus particles and a non-viral blending material in fiber form.

20. A method of converting virus particles to fiber form in which the virus particles retain their virus structure in the solid state comprising the step of spinning the viral particles into fiber form with a non-viral blending material while controlling concentration, viscosity, and optional use of electric field to control the fiber form and retain the virus structure after spinning.

21. A fibrous material comprising a plurality of fibers, wherein the fibers comprise one or more fiber spun, genetically engineered virus particles which retain a viral structure in the fiber state and have specific binding sites for binding to a conjugate material, wherein the conjugate material is a semiconductor material, a magnetic material, or a metallic material.

22. A fibrous material comprising a plurality of fibers, wherein the fibers comprise one or more fiber spun, genetically engineered virus particles which retain a viral structure in the fiber state and have specific binding sites for binding to a conjugate material, wherein the conjugate material is a crystalline material.

23. A fibrous material comprising a plurality of fibers, wherein the fibers comprise one or more fiber spun, genetically engineered virus particles which retain a viral structure in the fiber state and have specific binding sites for binding to a conjugate material, wherein the conjugate material is a drug or enzyme.

24. A fibrous material comprising a plurality of fibers, wherein the fibers comprise one or more fiber spun, genetically engineered virus particles which retain a viral structure in the fiber state and have specific binding sites for binding to a conjugate material, wherein the fibrous material further comprises polymeric material.

25. A woven material comprising the fibrous material of claim 9.

26. A sensor comprising the fibrous material of claim 9.

27. A biomedical device comprising the fibrous material of claim 9.

28. A drug delivery device comprising the fibrous material of claim 9.

* * * * *